US00PP16844P2

(12) United States Plant Patent
Evison et al.

(10) Patent No.: US PP16,844 P2
(45) Date of Patent: Jul. 18, 2006

(54) ***CLEMATIS* PLANT NAMED 'EVIPO005'**

(50) Latin Name: *Clematis viticella*
Varietal Denomination: EVIpo005

(75) Inventors: Raymond J. Evison, Guernsey (GB); Mogens N. Olesen, Fredensborg (DK)

(73) Assignees: Poulsen Roser A/S, Fredensborg (GB); Raymond J. Evison Ltd., Guernsey (GB)

( * ) Notice: Subject to any disclaimer, the term of this patent is extended or adjusted under 35 U.S.C. 154(b) by 175 days.

(21) Appl. No.: 10/351,415

(22) Filed: Jan. 24, 2003

(51) Int. Cl.
*A01H 5/00* (2006.01)

(52) U.S. Cl. ..... Plt./228
(58) Field of Classification Search ..... Plt./228
See application file for complete search history.

*Primary Examiner*—Kent Bell

(57) ABSTRACT

A new *Clematis* cultivar which is well suited to propagation in glasshouses with a tall growth habit, profuse, light green flowers, and continuous summer flowering. The variety successfully propagates from softwood cuttings and is suitable for cultivation in commercial glasshouses. This new and distinct variety has shown to be uniform and stable in the resulting generations from asexual propagation.

1 Drawing Sheet

Botanical classification: Genus: *Clematis*. Species: *viticella*.
Variety denomination: 'EVIpo005'.

SUMMARY OF THE INVENTION

The present invention constitutes a new and distinct variety of *Clematis* which originated from a controlled crossing of the female parent 'Venosa Vilocea', not patented, and the male parent 'EVIpure', not patented. The resulting seeds were planted in a controlled environment. The new variety is named 'EVIpo005'.

The new variety may be distinguished from the female parent, 'Venosa Violacea', by the following combination of characteristics:

1. 'Venose Violacea' has tepals which are Purple Group 77A to White Group 155A, while the claimed plant has tepals which are White 157D.
2. 'Venose Violacea' has anthers which are Purple 79A while the claimed plant does not develop complete flower parts.

The new variety may be distinguished from the female parent, 'EVIpure', by the following combination of characteristics:

The claimed plant posesses a central dome configuration of tepals while 'EVIpure' does not.

The objective of the hybridization of this *Clematis* variety for commercial nursery culture was to create a new and distinct variety with unique qualities, such as:

1. A very long flowering season;
2. Evergreen foliage if protected form frost;
3. Good flower longevity;
4. Continuous flowering.

These qualities required improvement in *Clematis* varieties that were in commercial cultivation and the objectives have been substantially achieved in the new variety, as evidenced by the unique combination of characteristics that are present in 'EVIpo005' which distinguish it from all other varieties of which we are aware.

The seeds from the hybridization were germinated and evaluations were conducted of the resulting *Clematis* plants in a controlled environment.

'EVIpo005' was selected by Raymond J. Evison and Mogens N. Olesen in their *Clematis* development program in Domarie Vineries Les Sauvagees, St. Sampsons, Guernsey, Channel Islands, United Kingdom in July, 1997.

Asexual reproduction of EVIpo005 by cuttings was first done by Raymond J. Evison and Mogens N. Olesen in Domarie Vineries Les Sauvagees, St. Sampsons, Guernsey, Channel Islands, United Kingdom in July, 1997. This initial and subsequent propagations have demonstrated that the characteristics of 'EVIpo005' are true to type and are transmitted from one generation to the next.

BRIEF DESCRIPTION OF THE DRAWING

The accompanying color illustration show as true as is reasonably possible to obtain in color photographs of this type:

1. Bloom, upper side;
2. Bloom, lower side;
3. Stem, leaves, bud at ¼ opening, bud closed;
4. Stem and leaves;
5. Stem and juvenile foliage.

DETAILED DESCRIPTION OF THE VARIETY

The following is a detailed description of 'EVIpo005', as observed in its growth throughout the flowering period in glasshouses at Domarie Vineries Les Sauvagees, St. Sampsons, Guernsey, Channel Islands, United Kingdom. The observed plant is grown within an unheated glasshouse in 2 liter containers. Plants are 2 years of age. Certain phenotypical characteristics of the variety may vary under different environmental, cultural, agronomic, seasonal, and climatic conditions. Color references are made using The Royal Horticultural Society (London, England) Colour Chart, 2001.

For a comparison, the nearest existing *Clematis* variety is 'EVIrida', described in U.S. Plant Pat. No. 15,093. Chart 1 details several physical characteristics of the 'EVIpo005' and the comparison variety.

CHART 1

| | 'EVIpo005' | 'EVIrida' |
|---|---|---|
| Quantity of tepals | More than 50. | 4 to 6. |
| Flower longevity as a cut flower | Long lasting | Short lived |
| Flower Center | Inner "ruff" of Green-White tepals. | Green bunch of sterile styles. |

Parents: 'Venosa Vilocea'×'EVIpure'.

FLOWER AND FLOWER BUD

Blooming habit: Continuous.
Flowering period: May through October.
Flower bud:
*Size.*—20 to 30 mm in length, 10 to 12 mm diameter.
*Bud form.*—Short, obovoid.
*Bud color.*—Yellow-Green Group 145B.
*Tepals.*—Yellow-Green Group 149D.
*Peduncle.*—Surface: Smooth. Length: 90 to 120 mm average length. Color: Green Group 137A. Strength: Horizontal.
*Receptacle.*—No receptacle observed.
*Borne.*—Compound cyme.
Flower bloom:
*Size.*—90 mm diameter, 10 to 25 mm in depth on average.
*Form.*—Globular.
*Color.*—Upon opening: Upper surface: Yellow-Green Group 145A to 149D. Lower surface: Yellow-Green Group 145A to 149D. After opening: Upper surface: White Group 157D. Lower surface: White Group 157D.
*Variations.*—Occasionally tepals will exhibit intonations of Purple Group 77A in the form of spots less than 0.5 mm in diameter.
*Fragrance.*—None.
*Lasting quality on plant.*—21 days.
Tepals:
*Tepal count.*—6 outer tepals, open flat, surrounding 50 or more inner tepals.
*Shape.*—Elliptic.
*Cross section.*—Flat.
*Undulation of margin.*—Weak.
*Margin.*—Entire.
*Tepal apex.*—Narrowly acute.
*Recurvature of tip.*—Outer tepals occasionally recurved.
*Persistence.*—Tepals drop off cleanly.
*Arrangement.*—Tepals are arranged regularly.
Reproductive organs: The claimed plant has no reproductive organs, and is completely sterile. The flower center is dominated by the globe of inner tepals.

PLANT

Plant form: Climbing and spreading.
Plant growth: Vigorous.
Height: Seasons growth attains meters 2 to 3 meters.
Spread: 1 to 2 meters.
Hardiness: Trials to date show the variety hardy in USDA Zones 6 to 9.
Stems:
*Color.*—Young wood: Green Group 137D, with intonations of Red Purple Group N70A. Older wood: Greyed Orange Group 165C.
*Internodes.*—Cylindrical. Length 130 to 180 mm.
*Petioles.*—Length: 30 to 60 mm. Color: Green Group 137C. Clasping: By winding leaf petiolus.
*Petiolule.*—Length 0 to 10 mm. Color: Green Group 137C.
*Bark.*—Young wood: Smooth. Older wood: Smooth.
Plant foliage: Evergreen. Can vary between 1) Trifoliate, 2) 3 ternate leaflets in pinnate form, or 3) 5 leaflets in pinnate form.
*Terminal leaflet size.*—40 mm length by 25 mm width.
*Simple leaf size.*—50 mm length by 30 mm width.
*Leaf shape.*—Cordate.
*Abundance.*—Average.
*Juvenile leaves.*—Upper side: Yellow Green Group 144A. Lower side: Yellow Green Group 144A.
*Mature leaves.*—Upper side: Green Group 137A. Lower side: Green Group 137C.
Plant leaves and leaflets:
*Stipules.*—Absent.
*Petiole.*—Length: 30 to 60 mm. Color: Green Group 137C. Underneath: Without prickles.
*Leaf edge.*—Terminal leaflet margin is entire.
*Shape.*—Base of leaflet: Acute. Apex: Acute.
*Texture.*—Thin. Upper side: Glabrous. Lower side: Ribbed.
*Surface.*—Matte finish.
Disease resistance: Subject to any disease that normally attacks the species, however the variety is more tolerant to Mildew than other *Clematis* known to us.

It is claimed:

1. A new and distinct variety of *clematis* plant, substantially as herein shown and described, as a distinct and novel *clematis* variety due to its abundant light green flowers with good keepability, attractive long lasting foliage and compact growth, year round flowering under glasshouse conditions, suitability for production from softwood cuttings in pots, durable flowers and foliage which make the variety suitable for distribution in the floral industry.

* * * * *

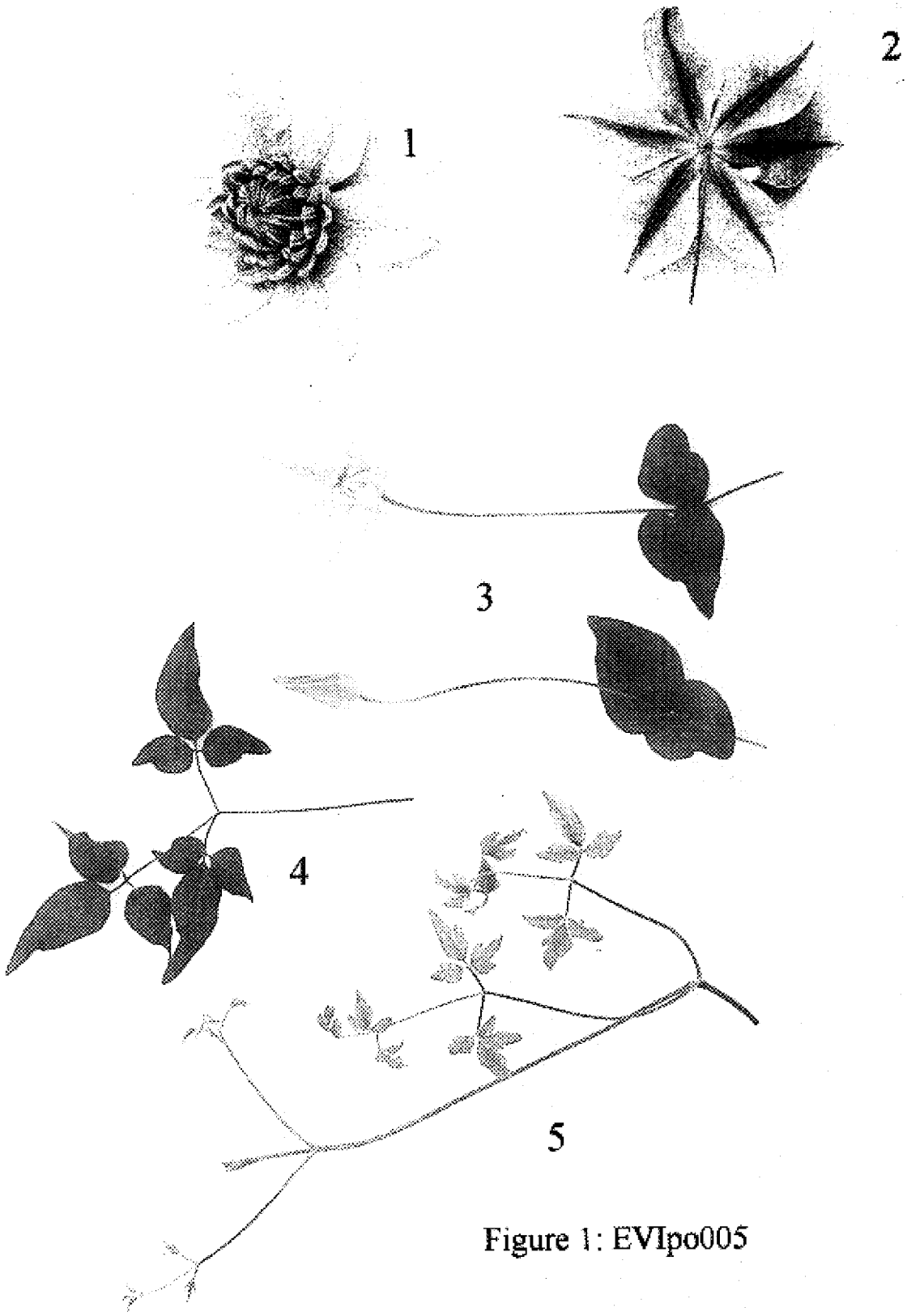
Figure 1: EVIpo005